US00PP10773P

United States Patent [19]

Krasinsky et al.

[11] Patent Number: Plant 10,773

[45] Date of Patent: Feb. 2, 1999

[54] BOXWOOD PLANT NAMED 'GREEN ICE'

[75] Inventors: Marlene Krasinsky, Brackenridge, Pa.; Robert E. Bayusik, deceased, late of Johnstown, Pa., by George Raptosh, legal representative

[73] Assignee: CP (Delaware) Inc., Wilmington, Del.

[21] Appl. No.: 962,669

[22] Filed: Nov. 3, 1997

[51] Int. Cl.[6] ..... A01H 5/00

[52] U.S. Cl. ..... Plt./54.1

[58] Field of Search ..... Plt./54.1

*Primary Examiner*—Howard J. Locker
*Assistant Examiner*—Melissa L. Kimball
*Attorney, Agent, or Firm*—Burns, Doane, Swecker & Mathis, L.L.P.

[57] ABSTRACT

A new and distinct Buxus cultivar of unknown parentage is provided that is believed to be an interspecific cross. The attractive medium-sized evergreen shrub exhibits a dense upright mounded and compact growth habit. No pruning is required to maintain the compact and mounded growth habit. The glossy foliage is deep olive green throughout the year and exhibits no substantial change in coloration during the winter. The winter hardiness also is exceptionally good. The new cultivar accordingly is capable of providing attractive ornamentation in the landscape even during the coldest winter months. No fragrance is emitted by the foliage. An unusually rapid growth cycle is possible following propagation which renders the new plant well suited for commercial production in containers.

2 Drawing Sheets

SUMMARY OF THE INVENTION

The present invention relates to a new and distinct Buxus cultivar that was discovered and selected during about 1964 at Portage, Pa. The exact parentage of the new cultivar is unknown. It is assumed that it may be an interspecific hybrid in view of the combination of characteristics exhibited by the new cultivar. Likely parents of the new cultivar are believed to be *Buxus sempervirens* 'Suffructicosa'×*Buxus microphylla korena* (i.e., Korean Box).

A single plant of the new cultivar was discovered, selected, and preserved having the distinctive characteristics discussed hereafter. Had the new cultivar of the present invention not been found and preserved, it would have been lost to mankind.

Upon careful observation and testing, the new cultivar of the present invention was found to express the following combination of characteristics:

(a) assumes a dense upright mounded and compact growth habit,
(b) forms deep olive green foliage throughout the year without any substantial coloration change during the winter,
(c) exhibits excellent winter hardiness to at least U.S.D.A. Plant — Hardiness Zone 4,
(d) lacks a typical Boxwood foliage fragrance, and
(e) exhibits an unusually rapid growth cycle following asexual propagation from a cutting.

The new cultivar is a dense upright mounded compact woody broad-leaf evergreen that is capable of being grown as an attractive ornamental plant throughout the entire year. The deep olive green coloration of the foliage is well maintained even during the winter and unlike many previously available Boxwood cultivars it well resists a tendency to assume a brownish-green foliage coloration during the winter. Good resistance to winter burn is exhibited. The hardiness of the new cultivar also equals or exceeds that of most previously known Boxwood cultivars that are known for superior hardiness. No blossoms or fruits have been observed to form on the new cultivar to date. Also, the foliage is found to be lacking in fragrance unlike typical Boxwood shrubs. Such absence of fragrance will be considered preferable by some growers.

The new cultivar can be grown to advantage as attractive ornamentation in the landscape, and is particularly well suited for use in the formation of low-growing hedges or edge plantings. No pruning is required to maintain the illustrated dense and compact growth habit. The new plant of the present invention commonly assumes a height that exceeds its width. Also, the new cultivar has been found to perform well in sun or shade in many soil types including those containing clay.

The new cultivar has been tested at Portage, Pa. since about 1964, at the Morton Arboretum at Lisle, Ill. since 1980, and at West Grove, Pa. since 1991.

When compared to the 'Green Velvet' cultivar (non-patented in the United States), the new 'Green Ice' cultivar exhibits a more upright growth habit, and unlike the 'Green Mountain' cultivar, the new 'Green Ice' cultivar exhibits a good retention of green foliage coloration during the entire year including the coldest winter months.

The rapid growth cycle of the new cultivar is particularly noteworthy. For instance, attractive compact plants produced from cuttings in two-gallon containers commonly assume a height of 1½ to 2 feet within two years following asexual propagation.

Asexual reproduction of the new cultivar by the use of cuttings has been carried out at Portage, Pa., and at West Grove, Pa. Such propagation has confirmed that the unique combination of characteristics of the new cultivar has been stably established and is well transmitted to successive generations.

The new cultivar has been named 'Green Ice'.

BRIEF DESCRIPTION OF THE PHOTOGRAPHS

The accompanying photographs show as nearly true as it is reasonably possible to make the same, in color illustrations of this character, typical specimens of the new cultivar.

FIG. 1 illustrates a mature plant of the 'Green Ice' cultivar during June 1990 while being grown in the landscape for test purposes at the Morton Arboretum, Lisle, Ill. The plant had been planted at the Morton Arboretum during the Spring of 1986. The uniform upright mounded and compact growth habit in the absence of pruning is illustrated.

FIG. 2 illustrates in the background at the left-center during June 1990, the same 'Green Ice' plant of FIG. 1. Typical Boxwood plants are shown in the foreground having lower more spreading growth habits combined with substantial winter damage. The 'Green Ice' plant is completely free of winter damage when grown under the same conditions.

FIG. 3 illustrates a young plant of the 'Green Ice' cultivar during the Spring of 1997 when growing in the landscape at West Grove, Pa. Such plant was originally grown in a container and was transplanted to the landscape during the Fall of 1996. The illustrated plant was approximately two years of age and had already assumed a height of approximately 1½ to 2 feet.

FIG. 4 illustrates a closer view of the typical old and new foliage of the 'Green Ice' cultivar during the Spring of 1997 that was formed on a young plant being grown in the landscape at West Grove, Pa. The attractiveness of the deep green spring flush is apparent.

DETAILED DESCRIPTION

Figure 1:
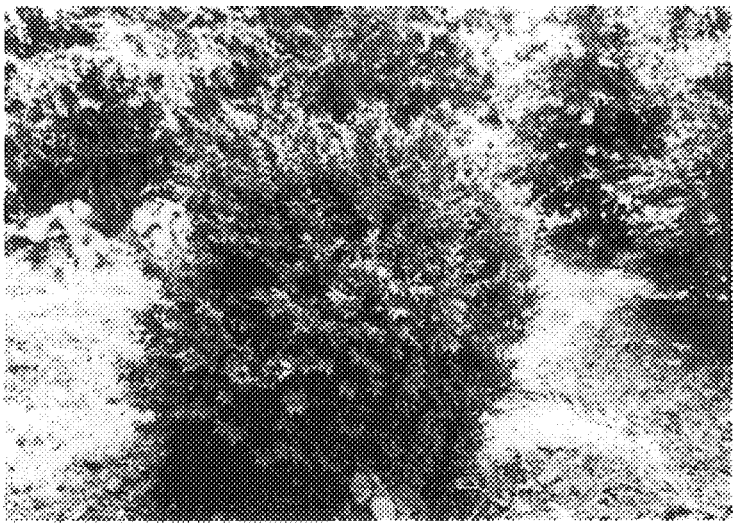
Figure 2:
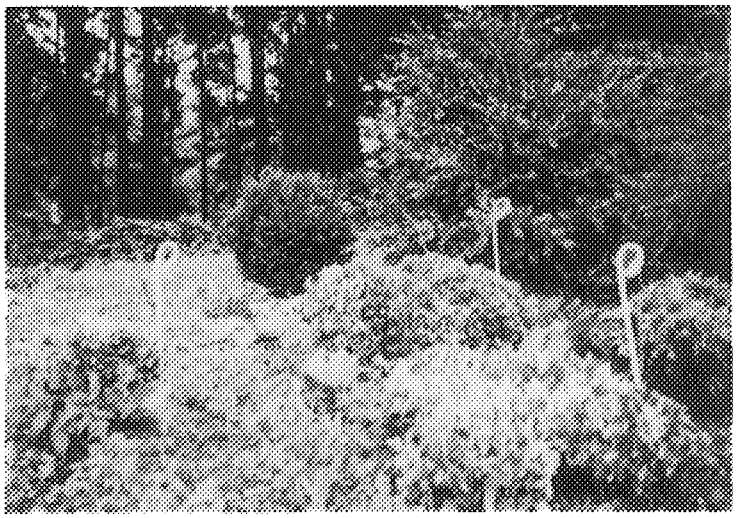
Figure 3:
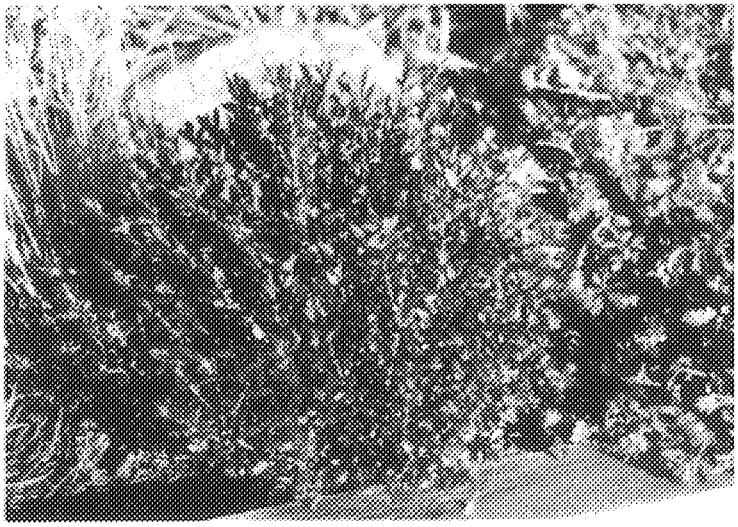
Figure 4:
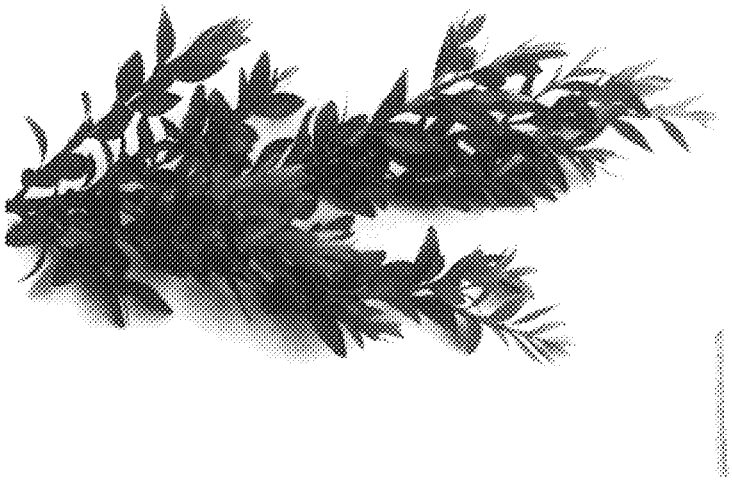

The following is a detailed description of the new cultivar of the present invention which was prepared while observing five year-old plants growing in containers at West Grove, Pa. Color terminology is in accordance with the R.H.S. Colour Chart of The Royal Horticultural Society, London, England, except where general terms of ordinary dictionary significance are used.

Type: Hardy broad-leafed evergreen shrub for garden decoration and general landscape use.

Botanical classification: Buxus hybrid, 'Green Ice' cultivar of unknown parentage.

Growth habit: Medium growing, dense, compact, and upright mounded. The plant height commonly exceeds the plant width. A more rapid growth cycle than most other Buxus cultivars commonly is observed.

Plant dimensions: A five year-old plant commonly assumes a height of approximately three feet and a width of approximately two feet, and a fully mature plant commonly assumes a height of approximately four feet and a width of approximately three feet.

Propagation: It holds its distinguishing characteristics through succeeding propagations by asexual propagation methods, such as the rooting of vegetative cuttings.

Juvenile foliage:

*Size.*—Approximately 2 cm. in length on average.

*Shape.*—Lanceolate with a cuneate base and an acuminate apex.

*Margin.*—Entire.

*Winter color.*—Upper surface: Yellow-Green Group 147A. Lower surface: Between Yellow-Green Group 144B and 144C with a midrib of Grayed-Yellow Group 161D.

*Spring color.*—Upper surface: Yellow-Green Group 144A. Lower surface: Yellow-Green Group 144C with veins of Yellow-Green Group 144A.

*Summer color.*—Upper surface: Green Group 139A. Lower surface: Yellow-Green Group 144A with margin of Green Group 137A, and a midrib of Yellow-Green Group 145A.

*Fragrance.*—None.

Mature foliage:

*Size.*—Approximately 2.5 cm. in length on average.

*Shape.*—Lanceolate with a cuneate base and an acuminate apex.

*Margin.*—Entire.

*Winter color.*—Upper surface: Yellow-Green Group 147A. Lower surface: Between Yellow-Green Group 146B and Yellow-Green Group 146C with a midrib of Grayed-Yellow Group 160D.

*Spring color.*—Upper surface: Yellow-Green Group 144A. Lower surface: Yellow-Green Group 144C with veins of Yellow-Green Group 144A.

*Summer color.*—Upper surface: Commonly between Green Group 137A and Green Group 139A. Lower surface: Yellow-Green Group 144A and 144B with a midrib of Yellow-Green Group 145C.

*Petioles.*—Size: Commonly approximately 0.25 cm. in length on average. Color: Yellow-Green Group 146D with highlights of Grayed-Orange Group 163C.

*Fragrance.*—None.

Juvenile branches:

*Color.*—Yellow-Green Group 144B with striations of Green Group 143B.

*Diameter.*—Approximately 0.25 cm. on average.

Mature branches:

*Color.*—Green Group 143C with striations of Grayed-Yellow Group 161C.

*Diameter.*—Approximately 1 cm. on average.

Inflorescence: No flower or fruit production has been observed to date.

Development:

*Hardiness.*—Is believed to be hardy to at least U.S.D.A. Plant — Hardiness Zone 4. The new cultivar has well withstood winter temperatures as low as −16° F. combined with significant wind forces at West Grove, Pa., with no sign of foliage burn.

*Disease resistance.*—No disease problems have been observed to date.

*Insect tolerance.*—No insect damage has been observed to date.

It is claimed:

1. A new and distinct variety of Buxus hybrid plant possessing the following characteristics:

(a) assumes a dense upright mounded and compact growth habit, (b) forms deep olive green foliage throughout the year without any substantial coloration change during the winter, (c) exhibits excellent winter hardiness to at least U.S.D.A. Plant — Hardiness Zone 4, (d) lacks a typical Boxwood foliage fragrance, and (e) exhibits an unusually rapid growth cycle following asexual propagation from a cutting;

substantially as herein shown and described.

* * * * *

UNITED STATES PATENT AND TRADEMARK OFFICE

CERTIFICATE OF CORRECTION

PATENT NO. : PP 10,773
DATED : February 2, 1999
INVENTOR(S) : Marlene Krasinsky et al.

It is certified that error appears in the above-identified patent and that said Letters Patent is hereby corrected as shown below:

Title page,
Item [54], Title, delete present title and insert -- BOXWOOD PLANT NAMED ´KRAZGREEN´ --.

Column 2,
Lines 17, 19, 33 and 38, delete "GreenIce" and insert -- "krazgreen" --

Column 3,
Lines 4, 7, 10, 18 and 32, delete "GreenIce" and insert -- "krazgreen" --

Signed and Sealed this

Twenty-first Day of September, 2004

JON W. DUDAS
*Director of the United States Patent and Trademark Office*